United States Patent [19]

Nilsson

[11] Patent Number: 5,130,544
[45] Date of Patent: Jul. 14, 1992

[54] OPTICAL GAS ANALYZER

[75] Inventor: Lars E. Nilsson, Sollentuna, Sweden

[73] Assignee: Gambro Engstrom AB, Sweden

[21] Appl. No.: 242,698

[22] Filed: Sep. 9, 1988

[30] Foreign Application Priority Data

Sep. 15, 1987 [SE] Sweden ................................. 8703564

[51] Int. Cl.$^5$ ............................................ G01N 21/61
[52] U.S. Cl. .................................... 250/343; 250/339;
250/345; 128/719; 356/437
[58] Field of Search .................... 250/343, 339, 504 R,
250/373, 345, 346; 356/437, 411, 414, 416, 419;
128/719

[56] References Cited

U.S. PATENT DOCUMENTS

| 3,860,344 | 1/1975 | Garfunkel | 250/345 |
| 3,941,487 | 3/1976 | Ehret et al. | 356/411 |
| 4,180,734 | 12/1979 | Gedeon | 250/373 |
| 4,271,124 | 6/1981 | Speeter | 250/343 |
| 4,320,297 | 3/1982 | Cederstrand et al. | 250/339 |
| 4,356,394 | 10/1982 | Cobean et al. | 250/347 |
| 4,423,739 | 1/1984 | Passaro et al. | 250/345 |
| 4,536,090 | 8/1985 | Schmidt et al. | 250/339 |
| 4,618,771 | 10/1986 | Farren | 250/345 |
| 4,749,276 | 6/1988 | Bragg et al. | 250/343 |
| 4,914,720 | 4/1990 | Knodle et al. | 250/343 |

FOREIGN PATENT DOCUMENTS 31783  3/1977  Japan ................................. 356/414

Primary Examiner—Carolyn E. Fields
Attorney, Agent, or Firm—Lerner, David, Littenberg, Krumholz & Mentlik

[57] ABSTRACT

Optical gas analyzers are disclosed for analyzing gas samples, including a source of radiation, a gas sample cell through which the radiation passes, a mirror for dividing that radiation into a number of secondary radiation paths for each of the gases in the gas sample which is to be analyzed, with the mirror being arranged so that after a single reflection from the mirror each of the secondary radiation paths is directed to an optical filter which passes a preselected wavelength characteristic of the particular gas in question, and then to a detector for measuring that wavelength characteristic. These optical gas analyzers are preferably used in connection with gas samples which include anesthetic gases, along with $CO_2$ and $N_2O$.

28 Claims, 2 Drawing Sheets

— AA-absorption
--- N₂O-absorption
—··— AA-filter transmission
—···— N₂O-filter transmission

OPTICAL GAS ANALYZER

FIELD OF THE INVENTION

The present invention relates to optical gas analyzers. More particularly, the present invention relates to optical gas analyzers which include a source of radiation and means for conducting the radiation through a gas sample and then to an optical filter. Still more particularly, the present invention relates to optical gas analyzers for the measurement of anesthetic gases such as halothane, isoflurane and enflurane, carbon dioxide and laughing gas ($N_2O$), particularly for monitoring patients and administering the anesthetic to those patients.

BACKGROUND OF THE INVENTION

Gas analyzers are currently found on the market which basically operate in accordance with four different principles:
  (a) Mass spectrometry;
  (b) Raman spectrometry;
  (c) IR-spectrometry; and
  (d) Change of mass of quartz crystals.

Mass spectrometers are rather expensive, but they are capable of rapidly measuring all of the gases, and of doing so with relatively good accuracy. They do, however, require qualified operators.

Raman spectrometers are also quite expensive, and their use in this field is relatively recent. Thus their quickness, accuracy and stability have not yet been documented. Furthermore, they also presumably require qualified operators.

The most commonly used such devices are the IR-based instruments. They are relatively cheap and stable, and do not require qualified operators. Their accuracy, however, depends on their design. For carbon dioxide and laughing gas ($N_2O$), the instruments presently on the market are sufficiently rapid for end-tidal measurements, but up to now these instruments have been too slow for anesthesia gases.

Instruments based on quartz crystals are very cheap. They exist, however, only for anesthesia gases. While they are rapid, they are unfortunately unstable, and have a rather short life. They also have limited accuracy, presumably because of the influence of laughing gas and water vapor thereon.

Measuring systems utilizing infrared detection are based upon the principle that the substance which is to be analyzed absorbs IR-radiation of wavelengths which are unique for the particular substance in question. In these systems, IR-radiation is generated by a source of radiation which continuously emits radiation over a large wavelength range. By means of an optical filter, for example, the correct wavelength is selected, and the radiation is then detected by an IR-detector which transduces the incident radiation energy to a proportional electrical signal. The choice of the analytical wavelength for the particular substance in question is very critical and wholly decisive in determining system characteristics such as accuracy and speed. In practice, this choice is governed by whether several of the substances present in a given sample absorb at or near the chosen wavelength, and whether it is technically and/or economically possible to measure radiation of this wavelength to the degree of accuracy required therefor.

Existing IR instruments for carbon dioxide and laughing gas ($N_2O$) have now been optimized to such a degree that improvements which can be translated into better performance for these substances do not appear to be possible.

For anesthesia gases, the situation is quite different. The absence of suitable commercial IR-detectors in this field has made it necessary for IR instruments for such gases to operate with short wavelengths, where these gases have very low absorption. This, in turn, has resulted in these instruments' requiring large sample volumes, and these instruments are therefore quite slow. Moreover, measurements made by these instruments have been disturbed by the presence of water vapor in the gases so analyzed.

For several years now, however, detectors have been on the market which allow for measurement at longer wavelengths, where the gases absorb much more strongly. Instruments which make use of these longer wavelengths therefore require very small sample volumes and are consequently far more rapid.

For end-tidal measurement the measuring system must somehow be provided with means to receive information indicating the approach of the end of the expiratory phase. This information can be obtained by measurement of the carbon dioxide content of the expired gas, and instruments which can thus measure the end-tidal carbon dioxide content have been known for a long time (e.g., capnometers, capnographs, etc.). On passage through the carbon dioxide meter, however, the sample gas becomes disturbed and an anesthesia gas meter coupled in series therewith will thus receive a phase-displaced and distorted sample. That is to say, any curves recorded thereby will have a distorted profile.

SUMMARY OF THE INVENTION

In accordance with the present invention, the deficiencies in the prior art have now been overcome by applicants' invention of an optical gas analyzer for the purpose of analyzing a number of gases in a gas sample and in which the optical gas analyzer includes a source of radiation means for defining a radiation path, gas sample means for providing the gas sample within the radiation path so that the radiation passes through the gas sample, radiation divider means for dividing the radiation after passing through the gas sample into a plurality of secondary radiation paths corresponding to the predetermined number of gases in the gas sample, a plurality of optical filter means corresponding to the predetermined number of gases, each of the optical filter means being characterized by passing therethrough a preselected wavelength characteristic of one of the predetermined number of gases to be analyzed, and a plurality of detector means corresponding to the predetermined number of gases for measuring the preselected wavelength characteristic of one of the predetermined number of gases to be analyzed.

In a preferred embodiment of the optical gas analyzer of the present invention, the radiation divider means comprises mirror means so that radiation can be passed through the optical filter means to the detector means after a single reflection from the mirror means.

In accordance with a preferred embodiment of the optical gas analyzer of the present invention, one of the gases is an anesthetic gas, and the corresponding optical filter means therefor are characterized by passing therethrough wavelengths only between 3.8 and 5$\mu$, and between 8 and 14$\mu$, so that moisture present in the anesthetic gas does not substantially affect the measured gas analysis therefor. Preferably, the gas sample also includes $CO_2$ and $N_2O$.

In accordance with another embodiment of the optical gas analyzer of the present invention, correction means are included for correcting the measured value measured by the detector means corresponding to the anesthetic gas caused by the presence of $N_2O$ as a function of the measured value measured by the detector means corresponding to the $N_2O$.

In accordance with another embodiment of the optical gas analyzer of the present invention, temperature control means are included for maintaining substantially constant the temperature of the gas sample means, the radiation divider means, the optical filter means, and the detector means. In a preferred embodiment, the temperature control means comprises envelope means surrounding the gas sample means, the radiation divider means, the optical filter means, and the detector means, and heating foil means in contact with the envelope. Preferably, the temperature control means includes gas sample temperature control means for controlling the temperature of a gas sample whereby the gas sample can be maintained at a substantially constant temperature above the dew point of any water vapor contained therein.

On an overall basis, the present invention thus relates to an optical gas analyzer which includes a source of radiation as well as means for conducting the radiation obtained from this source through a gas sample and through a number of optical filters corresponding to the number of gases to be analyzed, each of which allows through a wavelength which is representative of a particular one of those gases and specially absorbed by same, and then to a number of detectors corresponding to the number of gases to be analyzed. In this manner, the gas analyzers hereof employ means for dividing up the radiation path after it passes through the gas sample so as to obtain simultaneous measurement of the gas concentration in respective detectors.

The optical gas analyzers of the present invention are intended most particularly for measurement of anesthesia gases in the inspired and/or expired air of a patient. The optical filters are thus chosen so that they allow through wavelengths only of between 3.8 and $5\mu$ and 8 and $14\mu$; that is, without admitting any higher wavelengths, lower wavelengths, or intermediate wavelengths therebetween. In this manner, the moisture in the air which the patient is breathing does not affect the respective measurements obtained since water vapor has substantial absorption regions within those regions excluded by the above ranges. In measuring anesthesia gases, such as halothane, isoflurane and enflurane, a filter is preferably selected which is permeable for the wavelength $8.81\mu$, and in combination with an $N_2O$ filter and a $CO_2$ filter which are permeable for wavelengths specially absorbed by these gases, preferably $3.90\mu$ and $4.26\mu$, respectively.

It is noted, however, that the presence of $N_2O$ can affect the resultant measurements for the anesthesia gases, and for this reason correction means are provided to correct absorption caused by the $N_2O$ which is recorded by the anesthesia detector as a function of the measured value obtained in the $N_2O$ detector.

The above-described means for dividing the radiation path particularly consists of a mirror arrangement which preferably divides the radiation path into a number of equivalent ray bundles corresponding to the number of gases to be analyzed. It will be apparent to those skilled in this art, however, that other arrangements can also be used, such as collective optical lenses, provided that these allow through the particular wavelength involved.

In a particularly preferred embodiment of the present invention the gases to be analyzed are passed through a cell or the like with two windows, preferably made of $CaF_2$ (calcium fluoride), which are transparent for the radiation, and which are placed in the radiation path. Further examples of suitable materials which can be used include $BaF_2$ (barium fluoride), CdTe (cadmium telluride), Ge (germanium) and ZnS (zinc sulphide-Itran II).

In a particularly preferred embodiment of the optical gas analyzer of the present invention there is provided means for continuously conducting the gas mixture to be analyzed through the radiation path and means such as a rotating diaphragm for the regular interruption of the radiation path to obtain intermittent measuring values therefrom.

In monitoring patients during anesthetic treatment, it is important to determine the end-tidal measuring value of these respective gases. For this reason the gas analyzers hereof are provided with means for using the measured values obtained in the $CO_2$ detector to determine the end of the respective expiratory phase. For example, microcomputers included in the analyzer can be programmed to indicate the end of each expiratory phase.

The source of radiation employed in connection with the optical gas analyzer of the present invention preferably consists of an IR-source which continuously emits radiation over a large wavelength range, such as a thermal lamp with an envelope of quartz glass which absorbs the thermal radiation from the incandescent filament and in this manner is heated so that it in turn emits the desired radiation. This radiation can also be amplified within the desired wavelength range if the outermost heat source is surrounded by a thin metal envelope with a oxidized outer surface, such as an envelope of steel or brass, and preferably black-nickel-plated brass.

BRIEF DESCRIPTION OF THE DRAWINGS

The present invention can be more fully appreciated with reference to the following detailed description, which refers to the drawings in which.

DETAILED DESCRIPTION

Figure 1:
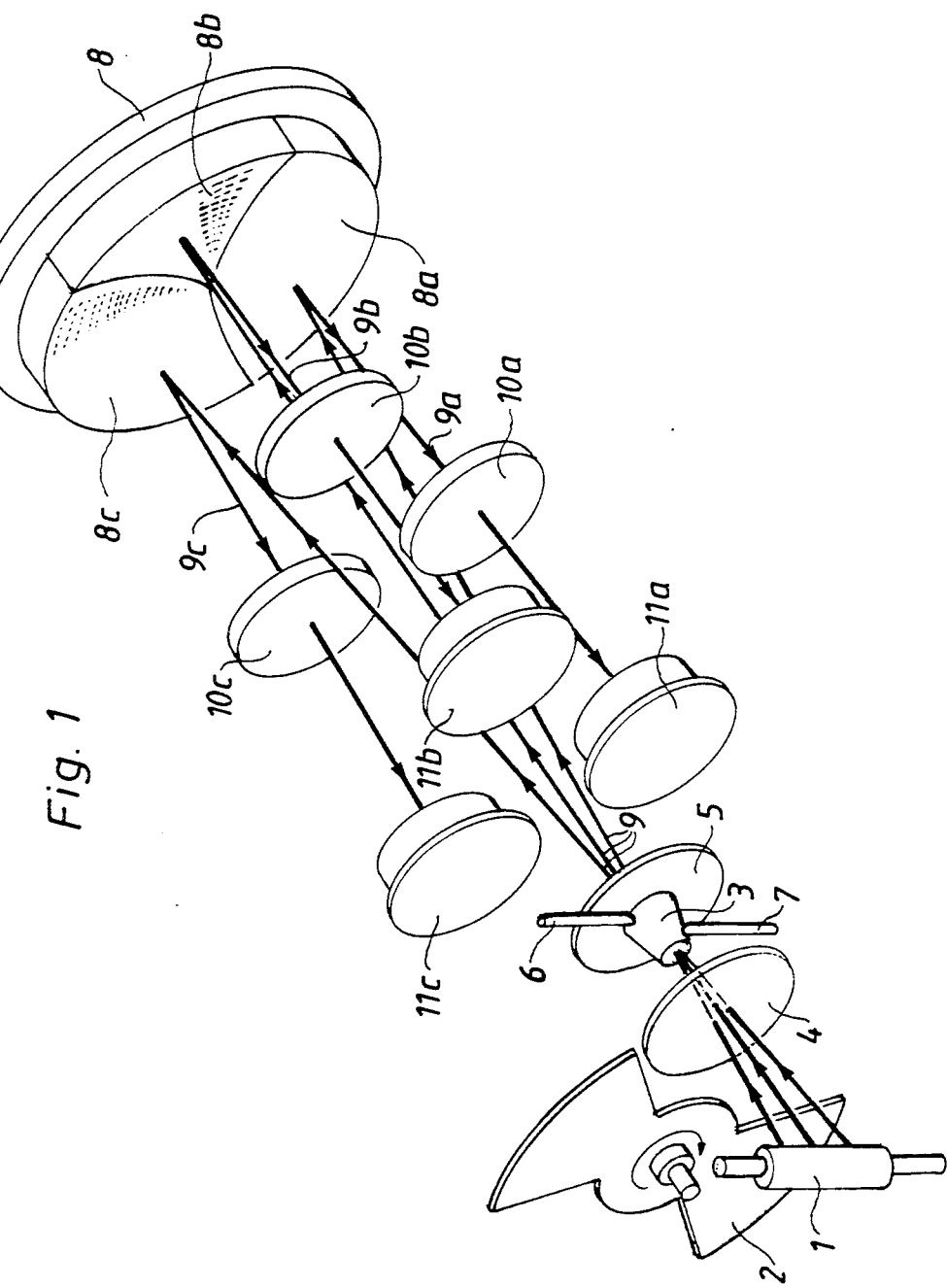
FIG. 1 is a schematic representation of the optical gas analyzer of the present invention showing the radiation path therein.

Referring to the Figures, in which like reference numerals refer to corresponding elements thereof, FIG. 1 shows a schematic illustration of the radiation path in a gas analyzer according to the present invention. On the left side of FIG. 1 there is shown a cylindrical light source 1, which may consist of a heated body, for example. The radiation from the light source 1 passes through a rotating diaphragm 2, which thus chops up the radiation in time (based on the detection principle). Thereafter the radiation passes through a conically shaped cell 3 which is defined by two windows, 4 and 5, which are transparent for the actual radiation. For reasons of clarity the window 4 is shown separate from the rest of the cell. Reference numeral 6 refers to an inlet for the gas mixture to be analyzed, and reference numeral 7 refers to an outlet means for same.

From cell 3, the radiation is then conducted to a three-part mirror 8, which divides up the original ray bundle 9 into three partial bundles, 9a, 9b and 9c, respectively, each of which is then directed through one of three filters, 10a, 10b and 10c, respectively, and further from these to one of three detectors, 11a, 11b and 11c, respectively.

When this gas analyzer is used for the measuring of anesthesia gases, the detector 11a preferable constitutes a $CO_2$ detector, and the filter 10a is of the type which allows through the representative wavelength for $CO_2$, namely $4.26\mu$. In the same manner, detector 11b may be an $N_2O$ detector, filter 10b thus being selected to allow through the representative wavelength for same, e.g., $3.90\mu$. Finally, detector 11c is used for the actual measurement of the anesthesia gas itself. Filter 10c is thus chosen so that it allows through a representative wavelength for same, e.g., $8.81\mu$.

In FIG. 1, for the sake of clarity, the different filters and detectors have been shown as separate units. Appropriately they can be constructed together as three units, i.e., with one unit for each wavelength.

Each portion 8a, 8b and 8c, respectively, of mirror 8 is designed as a 120° segment of a circle. Moreover, the portions of the mirror 8 have an "off-axis" placement in relation to the cuvette, whose window will therefore be pictured three times on the periphery of a circle. In this manner, the radiation can be easily conducted by the respective filter to the respective detector for simultaneous reading of the respective amounts of each gas in the sample.

For carbon dioxide there exists only one practically usable wavelength, namely $4.26\mu$. However, for $N_2O$, that is to say laughing gas, there are several such wavelengths. For technical reasons a wavelength of $3.90\mu$ is preferably utilized. For the three anesthesia gases there are a great number of wavelengths which may be used in principle. In order to avoid interference from water vapor, however, and to provide a test volume which is as small as possible, the preferred appropriate wavelength is $8.81\mu$. Moreover, this wavelength has the advantage that it can be used for the analysis of all three of the above-mentioned anesthesia gases. This, in turn, renders the design of this device much less expensive. This analysis is slightly disturbed, however, by laughing gas, so that the latter must be separately measured for purposes of compensation. The manner in which this compensation is carried out is described in more detail below. In addition, the content of laughing gas is also of direct clinical interest.

With regard to the detectors, until a few years ago measurements at wavelengths over $5\mu$ were practically impossible in this type of instrument, since suitable such detectors did not exist. The development of pyroelectric detectors has changed this situation, and rendered it possible to conduct such measurements at wavelengths where anesthesia gases strongly absorb the radiation.

Turning to the optical element used in this device, in order to measure the radiation at three wavelengths, that radiation, after passing the gas sample cell, must be divided over three filter/detector systems. A distinction may be made here between division in terms of time versus space. In accordance with this invention, spatial division is employed, and the three portions of the mirror each transmit their portion of the total radiation to their respective detectors.

The portions of the mirror 8 also collect the radiation from the IR source over a large solid angle. Since pyroelectric detectors create a considerable amount of noise, they require a strong signal. This is particularly important for the rapid detection which is required for end-tidal measurements. The amount of radiation which strikes the detector is directly proportional to the solid angle under which the detector "sees" the light source, or the angle under which the mirror collects the radiation. The three portions of the mirror are separate units on a functional basis, but may be manufactured as a single component, such as by the casting or compression molding of plastics, the diamond turning of aluminum or the pressing of glass.

As the source of radiation in the gas analyzer hereof a hot-body radiator is preferably used, which can consist of an ordinary 12 V/20 W halogen bulb run at approximately 12 W. The bulb envelope may consist of quartz glass, which absorbs all IR radiation from the incandescent wire and is thus heated thereby. The envelope, in turn, emits radiation of longer wavelengths, according to Planck's radiation law. It is thus the hot glass envelope which constitutes the actual radiation source. This source is already used in this form in a $CO_2$ analyzer, which is sold by the applicant under the name of ELIZA. Unfortunately, however, quartz has a relatively low coefficient of emission at the particular wavelengths in question, and the radiation source is therefore wholly ineffective, for example, at a wavelength of $8.8\mu$. Certain metal oxides, however, are known to have high coefficient of emission in the infrared spectrum. The efficiency of the source can thus be raised if the quartz envelope is surrounded by a thin metal envelope whose surface has been oxidized. This envelope may constitute a tube with a wall thickness of about 0.5 mm, which has been oxidized either in a flame or chemically. Successful experiments have been carried out with brass and stainless steel, both of which increased the radiation efficiency from about 2.5 to 2.7 times at $8.8\mu$, and approximately 1.5 times at $4.25\mu$. Corresponding improvements, and potentially even better results, should be obtainable with black-nickel-plated brass.

Figure 3:
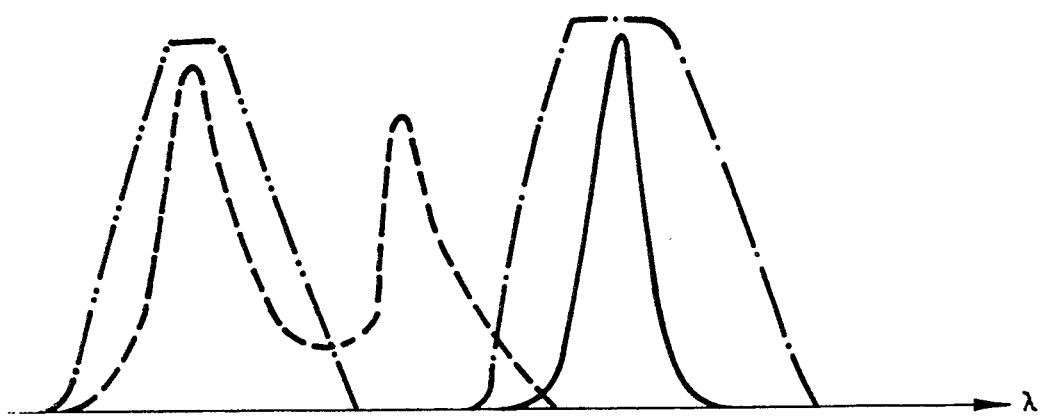
FIG. 3 is a graph of the absorption curves for $N_2O$, and for an anesthetic gas, as well as the transmission curves for the filters used for these gases in accordance with the present invention.

Referring next to FIG. 3, there is shown therein a schematic diagram illustrating the manner in which the laughing gas ($N_2O$) disturbs the analysis of the anesthesia gas (AA) where, for example, the anesthesia gas comprises halothane, isoflurane and enflurane. The filter which is thus used to isolate the wavelength range where the AA absorbs unfortunately allows through a small portion of one range where $N_2O$ also absorbs. A change in the $N_2O$ content will therefore affect transmission through the filter, and will thus be interpreted as a change in the AA content. This result therefore has to be corrected.

Such a correction is based on the following premises:

1. The $N_2O$ content is known, since it is being simultaneously measured in the $N_2O$ detector; and 2. The effect of $N_2O$ on the AA measurement can thus be quantitatively determined, for example, by calibration with a gas mixture of known $N_2O$ content.

The following is a technical description of how this compensation proceeds. For the sake of simplicity, a linear connection has been assumed here between the magnitudes of the absorbent and of the concentration.

Beer-Lambert-Law

Absorbance - $A_x = \log(I_o/I) = a_x \cdot [x]$; wherein $I_o$ represents the intensity with $O_2$ in the radiation path; I represents the intensity with sample in the radiation path; $a_x$ represents the calibration factor for the substance x; [x] represents the concentration of the substance x; and $A_x$ represents the absorbance for the substance x.

The absorbances are additive. If several substances absorb, we thus have the following:

$$A_{measured} = A_x + A_y + A_z \ldots$$

In the anesthesia channel (AA) the gases AA and $N_2O$ absorb, i.e., $$A^{AA}_{meas} = A^{AA}_{AA} + A^{AA}_{N_2O}$$

with the calibration factors $a^{AA}_{AA}$ and $a^{AA}_{N_2O}$, respectively*)

*)(Notation: $A^{channel}_{substance}$, $a^{channel}_{substance}$)

In the laughing gas channel, only $N_2O$ absorbs, i.e., $$A^{N_2O}_{meas} = A^{N_2O}_{N_2O}$$

with the calibration factor $a^{N_2O}_{N_2O}$

In the analysis of the material AA, it is [AA] which is desired, i.e., $$A^{AA}_{meas} = A^{AA}_{AA} + A^{AA}_{N_2O} \rightarrow A^{AA}_{AA} = A^{AA}_{meas} - A^{AA}_{N_2O} = a^{AA}_{AA}[AA]$$

but $$A^{AA}_{N_2O} = a^{AA}_{N_2O} \cdot [N_2O]$$

and $$[N_2O] = A^{N_2O}_{meas}/a^{N_2O}_{N_2O}$$

Therefore, $$\cdot [AA] = \frac{A^{AA}_{meas} - a^{N_2O}_{meas}\frac{a^{AA}_{N_2O}}{a^{N_2O}_{N_2O}}}{a^{AA}_{AA}}$$

Figure 2:
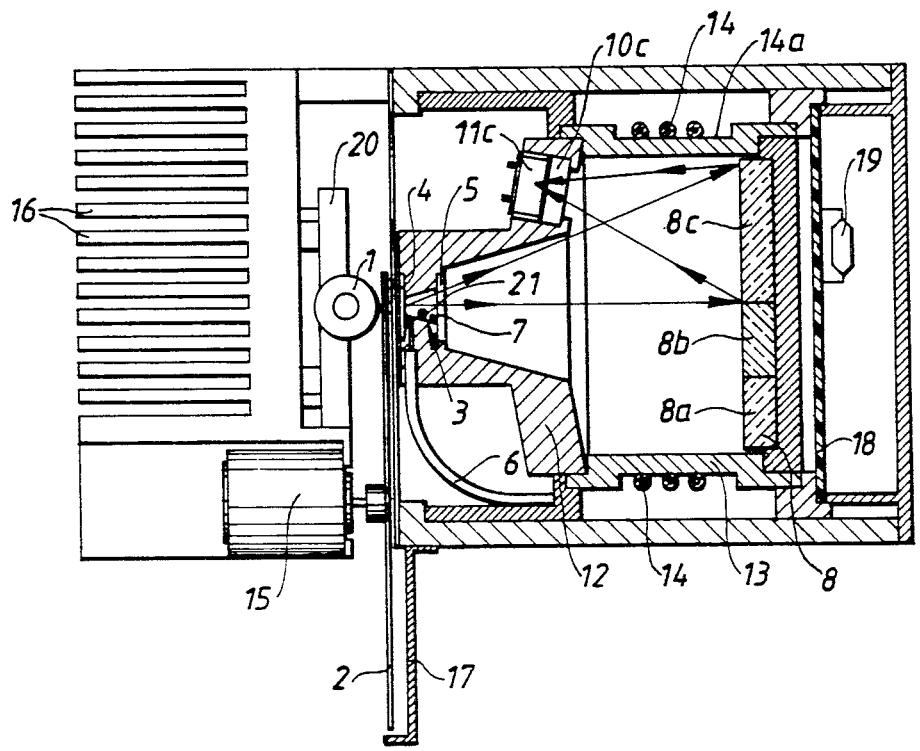
FIG. 2 is a side, elevational, partially sectional view of an optical gas analyzer in accordance with the present invention.

Referring next to FIG. 2, there is shown therein schematically, but in more detail, a practical embodiment of the subject matter of this invention. The light source is again designated 1, and the rotating diaphragm 2. In the same manner, the cell is designated 3, and its two windows 4 and 5, respectively. The gas mixture to be analyzed is introduced through inlet 6 and discharged through outlet 7. The mirror used has been designated 8, and it comprises portions 8a, 8b and 8c. The radiation path in this case has been designated only for the mirror portion 8c, which directs its portion of the radiation to detector 11c via filter 10c.

As shown in FIG. 2, mirror 8, filter 10c and detector 11c are arranged in a rigid envelope 12, which includes a distance tube 13, which makes it possible, among other things, to keep the temperature constant, as well as a precise position of the particular item. Around the distance tube 13 has been wound a thin heating foil 14a. This heats both the distance tube 13, as well as the items enclosed therein, and on the other hand a pipeline 14 for the gas being analyzed is wound outside the foil 14a, and is thus also heated to a suitable temperature. Numeral 15 designates the motor for rotating diaphragm 2, and numeral 16 designates a cooling flange. Numeral 17 designates protection for the diaphragm 2, and numeral 18 designates a circuit board, as symbolically indicated, which is connected to an amplifier 19. The circuit board 18 comprises, or is connected to, a microcomputer (not shown) for control of the desired measuring process. Numeral 20 finally designates a holder for the heat source 1, e.g., a standard ceramic holder. Finally, a pressure gauge arranged in the measuring cell is marked 21.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. An optical gas analyzer for analyzing an anesthetic gas, $N_2O$ and $CO_2$, each of said anesthetic gas, $N_2O$ and $CO_2$ having corresponding wavelength characteristics, contained in a gas sample comprising a source of radiation, means for defining a radiation path, gas sample means for providing said gas sample in said radiation path whereby said radiation passes through said gas sample, radiation divider means for dividing said radiation after passing through said gas sample into at least three secondary radiation paths, at least three optical filter means, said at least three optical filter means including first optical filter means corresponding to said anesthetic gas characterized by passing therethrough a wavelength of about $8.81\mu$, second optical filter means corresponding to said $N_2O$ characterized by passing therethrough a wavelength which is characteristic for said $N_2O$, and third optical filter means corresponding to said $CO_2$ characterized by passing therethrough only wavelengths of about $4.26\mu$, and at least three detector means for measuring said wavelength characteristics of said gases to be analyzed, said radiation divider means comprising mirror means wherein said at least three optical filter means and said mirror means are arranged such that said radiation may be passed through said at least three optical filter means to said at least three detector means after a single reflection from said mirror means.

2. The optical gas analyzer of claim 1 wherein said second optical filter means is characterized by passing therethrough only wavelengths of about $3.90\mu$.

3. The optical gas analyzer of claim 1 including correction means for correcting said wavelength characteristics measured by said at least three detector means corresponding to said anesthetic gas caused by the presence of said $N_2O$ as a function of the measured value measured by said at least three detector means corresponding to said $N_2O$.

4. The optical gas analyzer of claim 1 wherein said gas sample means includes cell means in said radiation path, and a pair of windows surrounding said cell means, said windows being transparent to said radiation.

5. The optical gas analyzer of claim 4 wherein said pair of windows comprises $CaF_2$.

6. The optical gas analyzer of claim 1 including temperature control means for maintaining substantially constant the temperature of said gas sample means, said radiation divider means, said at least three optical filter means, and said at least three detector means.

7. The optical gas analyzer of claim 6 wherein said temperature control means comprises envelope means surrounding said gas sample means, said radiation divider means, said at least three optical filter means, and said at least three detector means, and heating foil means in contact with said envelope means.

8. The optical gas analyzer of claim 6 wherein said temperature control means includes gas sample temperature control means for controlling the temperature of said gas sample whereby said gas sample can be maintained at a substantially constant temperature above the dew point of any water vapor contained therein.

9. The optical gas analyzer of claim 1 wherein said gas sample means includes gas sample conducting means for conducting said gas sample continuously through said radiation path.

10. The optical gas analyzer of claim 9 including interruption means for intermittently interrupting said radiation so as to obtain intermittent measuring values therewith.

11. The optical gas analyzer of claim 1 including control means for utilizing said wavelength characteristics reading of said detector means associated with said $CO_2$ for determining the end of an expiratory phase.

12. The optical gas analyzer of claim 1 wherein said source of radiation comprises a source of infrared radiation for continuously emitting said infrared radiation over a predetermined wavelength range.

13. The optical gas analyzer of claim 12 wherein said source of infrared radiation comprises a thermal lamp, and lamp envelope means comprising quartz glass for absorbing said radiation from said thermal lamp whereby upon heating said quartz glass emits said infrared radiation.

14. The optical gas analyzer of claim 13 wherein said envelope means includes a metallic outer layer including an oxidized outer surface.

15. The optical gas analyzer of claim 14 where said metallic outer layer comprises a material selected from the group consisting of steel and brass.

16. The optical gas analyzer of claim 15 wherein said metallic outer layer comprises nickel-plated brass.

17. The optical gas analyzer of claim 1 including pressure gauge means for measuring the pressure in said gas sample.

18. An optical gas analyzer for analyzing a predetermined number of gases contained in a gas sample comprising a source of infrared radiation for continuously emitting said infrared radiation over a predetermined wavelength range comprising a thermal lamp, lamp envelope means comprising quartz glass for absorbing said radiation from aid thermal lamp whereby upon heating said quartz glass emits said infrared radiation, said lamp envelope means including a metallic outer layer including an oxidized outer surface, means for defining an infrared radiation path, gas sample means for providing said gas sample in said infrared radiation path whereby said infrared radiation passes through said gas sample, infrared radiation dividing means for dividing said infrared radiation after passing through said gas sample into a plurality of secondary infrared radiation paths corresponding to said predetermined number of gasses, a plurality of optical filter means corresponding to said predetermined number of gases, each of said plurality of optical filter means characterized by passing therethrough a preselected wavelength characteristic of one of said predetermined number of said gases to be analyzed, and a plurality of detector means corresponding to said predetermined number of gases for measuring said preselected wavelength characteristic of one of said predetermined number of said gases to be analyzed, said radiation divider means comprising mirror means wherein said plurality of optical filter means and said mirror means are arranged such that said infrared radiation may be passed through said plurality of optical filter means to said plurality of detector means after a single reflection from said mirror means.

19. The optical gas analyzer of claim 18 wherein said metallic outer layer comprises a material selected from the group consisting of steel and brass.

20. The optical gas analyzer of claim 18 wherein said metallic outer layer comprises nickel-plated brass.

21. An optical gas analyzer for analyzing a predetermined number of gases contained in a gas sample comprising a source of radiation, means for defining a radiation path, gas cell means for providing said gas sample in said radiation path, whereby said radiation traverses said gas cell means directly from said source of radiation without prior reflection, radiation divider means for dividing said radiation after traversing said gas cell means into a plurality of secondary radiation paths corresponding to said predetermined number of gases, a plurality of optical filter means corresponding to said predetermined number of gases, each of said plurality of optical filter means characterized by passing therethrough a preselected wavelength characteristic of one of said predetermined number of gases to be analyzed, and a plurality of detector means corresponding to said predetermined number of gases for measuring said preselected wavelength characteristic of one of said predetermined number of said gases to be analyzed, said radiation divider means comprising mirror means wherein said source of radiation, said plurality of optical filter means and said mirror means are arranged such that said radiation may be passed from said source of radiation directly to said mirror means and through said plurality of optical filter means to said plurality of detector means with only a single reflection.

22. The optical gas analyzer of claim 21 wherein said source of radiation comprises a source of infrared radiation for continuously emitting said infrared radiation over a range of wavelengths including $8.81\mu$.

23. The optical gas analyzer of claim 22 wherein one of said plurality of optical filter means is characterized by passing therethrough wavelengths of about $8.81\mu$.

24. The optical gas analyzer of claim 21 wherein said analyzer comprises means for analyzing an anesthetic gas, and wherein one of said plurality of optical filter means is characterized by passing therethrough a wavelength of between about 3.8 and $5\mu$ or between about 8 and $14\mu$, whereby moisture present in said anesthetic gas does not substantially affect the measured gas analysis therefrom.

25. An optical gas analyzer for analyzing a predetermined number of gases contained in a gas sample comprising a source of infrared radiation, means for defining a radiation path, gas sample means for providing said gas sample in said radiation path whereby said radiation passes through said gas sample directly from said source of radiation without prior reflection, radiation divider means for dividing said radiation after passing through said gas sample into a plurality of secondary radiation paths corresponding to said predetermined number of gasses, said radiation divider means being disposed with respect to said source of radiation and said gas sample means whereby said radiation passes to said radiation divider means directly from said radiation source and said gas sample means without prior reflection, a plurality of optical filter means corresponding to said predetermined number of gases, each of said plurality of optical filter means characterized by passing therethrough a preselected wavelength characteristic of one of said predetermined number of said gases to be analyzed, and a plurality of detector means corresponding to said predetermined number of gases for measuring said preselected wavelength characteristic of one of said predetermined number of said gases to be analyzed, said radiation divider means comprising mirror means wherein said plurality of optical filter means and said mirror means are arranged such that said infrared radiation may be passed through said plurality of optical filter means to said plurality of detector means after a single reflection from said mirror means.

26. An optical gas analyzer for analyzing a predetermined number of gases including an anesthetic gas contained in a gas sample comprising a source of radiation, means for defining a radiation path, gas sample means for providing said gas sample in said radiation path whereby said radiation passes through said gas sample, radiation dividing means for dividing said radiation after passing through said gas sample into a plurality of secondary radiation paths corresponding to said predetermined number of gases, a plurality of optical filter means corresponding to said predetermined number of gases, said plurality of optical filter means including first optical filter means corresponding to said anesthetic gas characterized by passing therethrough a wavelength only between about 3.8 and $5\mu$ or between about 8 and $14\mu$, whereby moisture present in said anesthetic gas does not substantially affect the measured gas analysis therefor, and a plurality of detector means corresponding to said predetermined number of gases for measuring preselected wavelength characteristics of said predetermined number of said gases to be analyzed, said radiation divider means comprising mirror means wherein said plurality of optical filter means and said mirror means are arranged such that said radiation may be passed through said plurality of optical filter means to said plurality of detector means after a single reflection from said mirror means.

27. The optical gas analyzer of claim 26 wherein said analyzer comprises means for analyzing $N_2O$, and wherein one other of said plurality of optical filter means is characterized by passing therethrough only wavelengths of about $3.90\mu$.

28. The optical gas analyzer of claim 26 wherein said analyzer comprises means for analyzing $CO_2$, and wherein one other of said plurality of optical filter means is characterized by passing therethrough only wavelengths of about $4.26\mu$.

* * * * *

UNITED STATES PATENT AND TRADEMARK OFFICE
CERTIFICATE OF CORRECTION

PATENT NO. : 5,130,544
DATED : July 14, 1992
INVENTOR(S) : Lars E. Nilsson

It is certified that error appears in the above-indentified patent and that said Letters Patent is hereby corrected as shown below:

Column 9, line 61, "aid" should read --said--.

Column 10, line 23, delete "18" and insert therefor --19--.

Signed and Sealed this

Fourteenth Day of September, 1993

Attest:

BRUCE LEHMAN

Attesting Officer     Commissioner of Patents and Trademarks